US005537995A

United States Patent [19]

Ottestad

[11] Patent Number: 5,537,995

[45] Date of Patent: Jul. 23, 1996

[54] BREATHING SYSTEM HAVING BREATHING BAG AND SUPPLEMENTAL GAS DOSING CONTROLS

[75] Inventor: Nils T. Ottestad, Tønsberg, Norway

[73] Assignee: Den Norske Stats Oljeselskap A.S., Stavanger, Norway

[21] Appl. No.: 329,784

[22] Filed: Oct. 27, 1994

Related U.S. Application Data

[63] Continuation of Ser. No. 930,611, filed as PCT/NO91/00052, Apr. 2, 1991, published as WO91/15265, Oct. 17, 1991, abandoned.

[30] Foreign Application Priority Data

Apr. 30, 1990 [NO] Norway .................................. 901521

[51] Int. Cl.$^{6}$ .............................. A62B 9/02; A62B 7/04; A61M 16/00; F16K 31/26

[52] U.S. Cl. .............................. 128/204.28; 128/204.26; 128/205.24

[58] Field of Search ........................ 128/204.15, 204.26, 128/204.28, 204.29, 205.14, 205.16, 205.22–205.25

[56] References Cited

U.S. PATENT DOCUMENTS

| | | | |
|---|---|---|---|
| 1,225,269 | 5/1917 | Paul et al. | 128/204.28 |
| 4,300,547 | 11/1981 | Pasternack | 128/204.15 |
| 4,364,384 | 12/1982 | Warncke et al. | 128/204.28 |
| 4,567,889 | 2/1986 | Lehmann | 128/204.28 |
| 4,608,976 | 9/1986 | Suchy | 128/205.24 |
| 4,667,669 | 5/1987 | Pasternack | 128/204.28 |
| 4,793,340 | 12/1988 | Ottestad | 128/200.24 |
| 4,886,056 | 12/1989 | Simpson | 128/204.21 |
| 5,036,841 | 8/1991 | Hamilton | 128/205.17 |
| 5,072,728 | 12/1991 | Pasternack | 128/205.22 |
| 5,076,267 | 12/1991 | Pasternack | 128/205.22 |

FOREIGN PATENT DOCUMENTS

| | | |
|---|---|---|
| 0087034 | 8/1983 | European Pat. Off. . |
| 928810 | 6/1955 | Germany . |
| 3105637 | 9/1982 | Germany . |
| 389073 | 10/1976 | Sweden . |
| 389072 | 10/1976 | Sweden . |
| 448519 | 3/1987 | Sweden . |
| 2236254 | 4/1991 | United Kingdom . |

*Primary Examiner*—Kimberly L. Asher
*Attorney, Agent, or Firm*—Banner & Allegretti, Ltd.

[57] ABSTRACT

A closed or semi-closed breathing system for smoke diving and the like includes a pneumatically controlled breathing bag (1) communicating in a circulation (4, 5, 6) with a breathing mouthpiece or breathing mask (2) for a user and with an absorption means (3) for exhaled $CO_2$, a pneumatic actuator (9) arranged for alternating expansion and contraction of the breathing bag (1) in accordance with the breathing pattern of the user, and a pressurized gas source (11) coupled to the breathing bag (1) to supplement the breathing gas therein. The system includes a mode regulator (10) arranged to control the actuator's actuation of the breathing bag (1) while simultaneously maintaining an overpressure in the breathing mask (2) in relation to the surroundings, and a dosing means (13) for the supply of a metered gas quantity to the breathing bag (1) in dependence on its degree of filling.

17 Claims, 3 Drawing Sheets

BREATHING SYSTEM HAVING BREATHING BAG AND SUPPLEMENTAL GAS DOSING CONTROLS

This application is a continuation of application Ser. No. 07/930,611, filed as PCT/NO91/00052, Apr. 2, 1991, published as WO91/15265, Oct. 17, 1991, now abandoned.

BACKGROUND OF THE INVENTION

The present invention relates to a closed or semi-closed breathing system for smoke diving and the like, comprising a pneumatically controlled breathing bag communicating in a circulation circuit with a breathing piece (e.g., mouthpiece or breathing mask) for application to the face of a user and with an absorption means for exhaled $CO_2$, a pneumatic actuator arranged for alternating expansion and contraction of the breathing bag in accordance with the breathing pattern of the user, and a pressurized gas source coupled to the breathing bag to supplement the breathing gas therein.

There are known a number of embodiments of self-contained breathing systems. Breathing equipment for smoke diving (e.g., fire fighting operations wherein a fire fighter "dives" into an environment containing smoke and toxic gases) preferably is based on the supply of breathing gas through a breathing valve, whereas exhaled gas is "dumped" directly to the surroundings through a one-way valve ("open breathing system"). Alternative types of breathing equipment are based on recovery of exhaled gas in a "closed" or "semi-closed" circulation. This implies that exhaled gas—partly or completely—is purified of $CO_2$ and supplied with oxygen so that it is again suitable as a breathing gas. With closed or semi-closed breathing systems there is achieved a long service life with a moderate gas supply, but they are normally difficult to breathe with because of the fact that the gas is recirculated by lung force. In comparison, good open breathing systems are easy to breathe with, but have a considerably shorter service life since one must be concerned with keeping the weight of the apparatus low. A substantial advantage with open breathing systems is that one is able to maintain a safety pressure (weak overpressure) in the breathing mask, so that the ingress of gases which are harmful to the user's health, is prevented.

SUMMARY OF THE INVENTION

The object of the invention is to provide a closed or semi-closed breathing system which has a safety overpressure in the breathing mask and which utilizes the available breathing gas reservoir optimally, and wherein the system is reliable in service, is simple and reasonable to produce, and has a low weight and a long service life.

According to the invention there is provided a breathing system of the type stated in the introduction which is characterized in that it includes a mode regulator arranged to control the actuator's actuation of the breathing bag while simultaneously maintaining an overpressure in the breathing mask in relation to the surroundings, and a dosing means for the supply of a metered gas quantity to the breathing bag in dependence on the degree of filling of the bag.

In the present breathing system a small breathing effort is required in that the pressure energy of the supplied oxygen is used to assist the recirculation of the breathing gas, the oxygen supply taking place through the pneumatic actuator which alternatingly expands and contracts the breathing bag in accordance with the breathing pattern of the user. This is a technique which is already used in a semi-closed breathing system for underwater diving, and in this connection reference is made to U.S. Pat. No. 4,793,340. The technique has, however, not been previously used in a closed breathing system. In the present breathing system it is an important point that this technique is utilized to establish a "safety pressure" in the breathing mouthpiece or breathing mask of the user, something which prevents the ingress of gases which are harmful to the user's health. This is of great importance as viewed from the safety point of view, and is—as far as applicant knows—not achieved in any other self-contained closed breathing system.

In the breathing system according to the invention, the mode regulator sees to it that the actuator is supplied with compressed oxygen, or alternatively that supplied oxygen is "vented" to the breathing bag which thereby controls the recirculation of breathing gas, at the same time as it is ensured that a small safety overpressure is maintained in the breathing mask during inhalation as well as during exhalation. The actuator is so dimensioned that the oxygen quantity received thereby and thereafter "vented" to the breathing bag, is somewhat smaller than the quantity absorbed in the respiration. It is therefore necessary to inject a certain oxygen quantity directly into the circulation of the system, to maintain the oxygen level in the breathing gas. According to the invention, this is achieved in that the dosing means is arranged to discharge a metered quantity of gas into the breathing bag each time when, during exhalation, there is not achieved a sufficient filling of the breathing bag. Thus, the system is not, like many other closed oxygen apparatus, based on a fixed injection of gas rich in oxygen, but utilizes the available gas reservoir optimally. It has been found to be advantageous to dimension the system so that the maximum driving pressure of the actuator is approximately ±15 cm water column. In practice this implies that the actuator is able to compensate for the work which the lungs of the user otherwise would have to carry out in order to overcome restrictions through one-way valves, hoses, $CO_2$ absorber, etc. in the system.

An advantageous embodiment of the system according to the invention is characterized in that the circulation circuit of the system includes conduit stretches of which the outer surfaces are covered by a relatively thick porous material which, saturated with water, utilizes the evaporation of the water for cooling down the breathing gas circulating in the circulation circuit during operation.

The breathing system then is constructed in such a manner that surrounding gas flows past the surface and causes an efficient evaporation. The evaporation heat is partly taken from the wet surface which is cooled down considerably. Further, the wet surfaces of the conduit stretches and possible other cooled-down surfaces in the system have a good thermal conduction to internal surfaces of the breathing system, so that an efficient cooling of the breathing gas is achieved. Such an arrangement for cooling of the breathing gas is advantageous as compared to traditional breathing systems wherein the temperature of inhaled gas may be well above the body temperature. In addition, this solution has the advantage that the evaporation increases with the surrounding temperature, so that the system manages to maintain an acceptable breathing gas temperature even in rather warm surroundings. Another advantage of this solution is that wetting with water is convenient in a fire fighting environment. The system is easily made ready for operation by, e.g., immersion in a container of water. A thick porous material will be able to absorb a considerable quantity of water, and the cooling therefore can take place over a relatively long time without another wetting of the porous material.

BRIEF DESCRIPTION OF THE DRAWINGS

The invention will be further described below in connection with an exemplary embodiment with reference to the drawings, wherein.

DETAILED DESCRIPTION OF THE PREFERRED EMBODIMENTS

Figure 1:
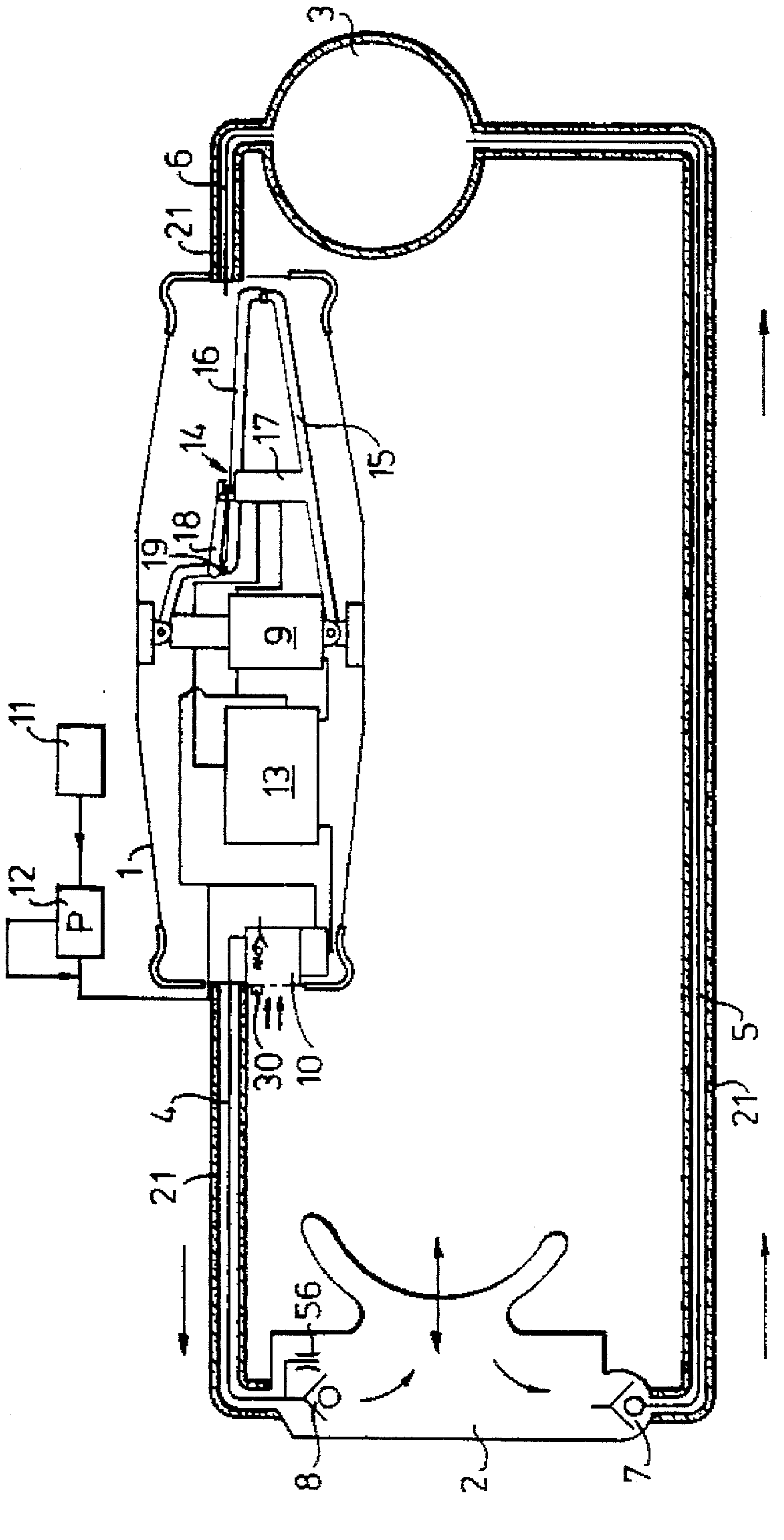
FIG. 1 shows a schematic view, partly in section, of a preferred embodiment of a breathing system according to the invention.

The embodiment shown in FIG. 1 constitutes a closed breathing system wherein a breathing bag 1, a breathing mask 2 and a $CO_2$ absorbing means 3 are connected in series in a closed circulation circuit, said units being interconnected through conduit lengths 4, 5 and 6. The breathing gas is inhaled from the breathing bag 1 through the breathing mask 2 which is provided with one-way valves 7 and 8 ensuring that inhaled and exhaled gases are not mixed. Exhaled gas passes via the means 3, which consists of a container containing a $CO_2$ absorbing material, into the breathing bag 1.

Within the breathing bag 1 there is arranged a pneumatic actuator 9 consisting of a cylinder/piston unit (see FIG. 3) which, as shown, is articulated to the side walls of the breathing bag in the central region thereof. The actuator causes alternating expansion and contraction of the breathing bag in accordance with the breathing pattern of the user, as further described below. For the control of the actuator 9, there is provided a mode regulator 10 seeing that the actuator is supplied with compressed oxygen, or alternatively that supplied oxygen is vented to the breathing bag, as also further described below. Pressurized oxygen is supplied from a source 11 through a pressure reducing valve 12.

In the illustrated embodiment, the actuator 9 is dimensioned such that the oxygen quantity which is received and thereafter vented to the breathing bag, is somewhat smaller than the quantity absorbed in the user's respiration. In order to maintain the oxygen level in the breathing gas, it is therefore necessary to inject a certain oxygen quantity directly into the circulation. For this purpose there is provided a dosing means 13 which is arranged to discharge a metered oxygen quantity into the breathing bag 1 each time when, during exhalation, there is not achieved a sufficient filling of the breathing bag.

In order to record the filling degree of the breathing bag in each exhalation (expansion of the breathing bag), there is provided a sensing means 14 in combination with a pair of arms 15, 16 following the movement of the breathing bag, the arms at one of their ends being pivotally connected to each other, and at their other ends being articulated to the side walls of the breathing bag at the same places where the actuator 9 is coupled to the breathing bag. The sensing means comprises a holding member 17 fixed to one arm 15 and extending in the direction of and past the other arm 16, a lever 18 pivotally connected to the free end of the holding member, a transverse pin 19 fixed to the arm 16 and cooperating with the lever 18, and a valve 20 (see FIG. 3) provided in the holding member and arranged to be actuated by the lever 18. This valve is opened when the lever 18 is lifted by the transverse pin 19 when the breathing bag 1 is filled beyond a certain filling degree, and then delivers a "blocking signal" to the dosing means 13, as further described below.

As appears from FIG. 1, the outer surfaces of the conduit lengths 4, 5, 6 are covered by a relatively thick layer of a material 21 which is porous and water-absorbing, and which—in operation—is intended to be saturated with water, the water then evaporating and providing for cooling-down of the breathing gas circulating in the circulation, as discussed above. Also the container 3 is covered by the water-absorbing material, and in particular those parts of the circulation located downstream of the container 3, may be extended in a suitable manner, with a view to achieving a large, efficient evaporation surface to the surrounding atmosphere.

Figure 2:
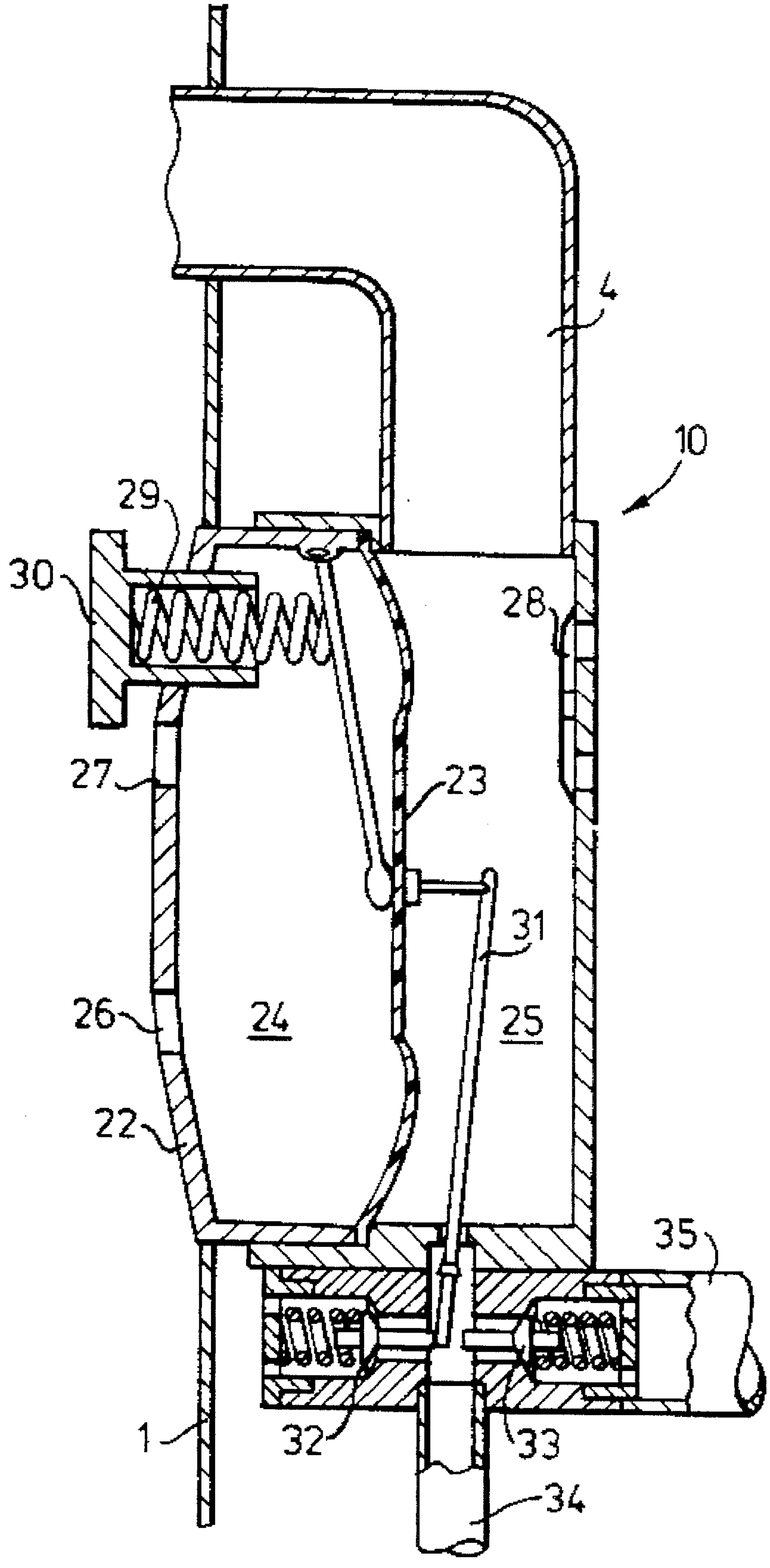
FIG. 2 shows a sectional view of the mode regulator in FIG. 1 on an enlarged scale.

The construction of the mode regulator 10 is shown in more detail in FIG. 2. It consists of a housing 22 containing a sensing diaphragm 23 dividing the housing into a pair of chambers 24, 25. The chamber 24 communicates with the outer atmosphere through a pair of apertures 26, 27, whereas the chamber 25 communicates with the breathing mask 2 through the conduit 4 and is supplied with breathing gas from the breathing bag 1 through a one-way valve 28. In the chamber 24 there is provided a spring 29 for acting upon the sensing diaphragm 23, so that in operation it is affected by a certain spring force in addition to the atmosphere pressure in the chamber 24. In this manner there is achieved a certain overpressure or safety pressure in the system, when the spring is activated. The spring 29 is arranged in a cap 30 which is screwed into the housing 22 and can be screwed in to a greater or smaller extent, for setting of a desired spring prestressing force and thereby a desired overpressure. It is obvious that the diaphragm-influencing means may be carried out in many other ways than the illustrated spring and cap, but it is essential that the means is easily accessible to the user.

Figure 3:
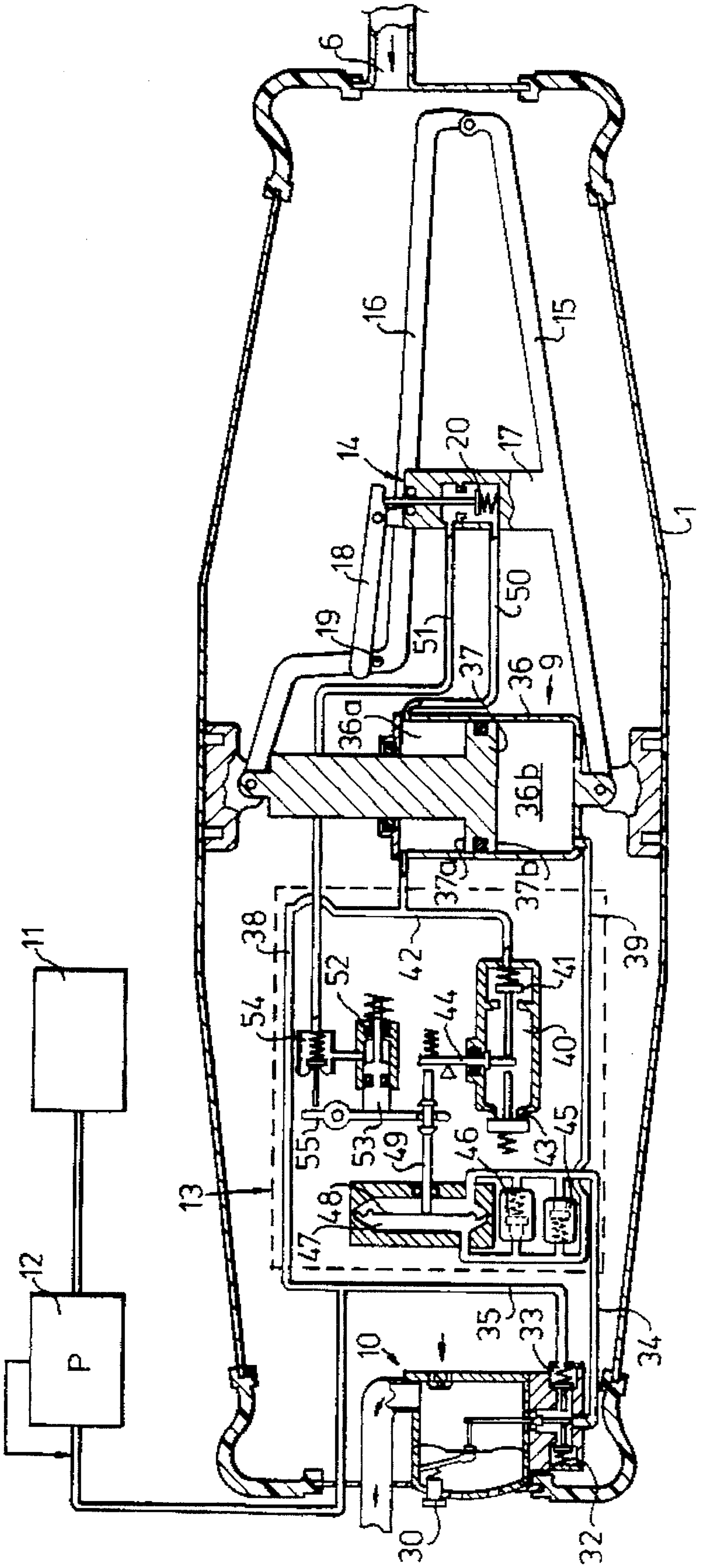
FIG. 3 shows an enlarged sectional view of the breathing bag in FIG. 1, the Figure showing more detailed sectional views of the elements and units arranged within the breathing bag.

The sensing diaphragm 23 is mechanically coupled to a lever 31 for alternative actuation of a first and a second valve 32 and 33, respectively, of which a first valve 32 communicates with the actuator 9 through a conduit 34, and the second valve 33 is coupled to a conduit 35 communicating with the pressurized gas source 11 (through the reducing valve 12) as well as with the actuator 9, as shown in FIG. 3.

The construction of the actuator 9 and the dosing means 13 is shown more in detail in FIG. 3.

As shown, the actuator 9 consists of a cylinder 36 and a piston 37 having, as viewed in FIG. 3, an upper pressure surface **37*a* which is substantially smaller than the lower pressure surface 37*b* of the piston. The upper cylinder compartment 36*a* is connected to the pressurized gas source 11 through a conduit 38, and the lower cylinder compartment 36*b* is connected to the valves 32, 33 of the mode regulator through a conduit 39 (passing through the dosing means 13) and the conduit 34. Thus, the smallest pressure surface 37*a* of the piston stands under a constant pressure influence from the pressurized gas source 11, so that the pressure direction of actuator 9 changes as its lower cylinder compartment 36*b* is supplied with gas from the pressurized gas source (through the mode regulator valve 33) or is vented (through the valve 32**). As an alternative to connecting the pressurized gas source to the upper cylinder compartment, the upper side of the piston instead might be acted upon by a continuously acting spring force.

The dosing means 13 includes a small gas reservoir 40 which is arranged to be filled with oxygen through a first valve or inlet valve 41 which is connected to the pressurized gas source 11 through a conduit 42 and the conduit 38, and further is arranged to be discharged into the breathing bag through a second valve or outlet valve 43. The valves 41 and 43 are arranged to be opened and closed alternately by an operating means in the form of a spring-loaded lever 44 which, in its initial position, keeps the valve 41 open. In the conduit 39 between the valves 32, 33 of the mode regulator 10 and the lower cylinder compartment of the actuator 9, there is connected a unit consisting of a pair of spring-loaded and oppositely directed one-way valves 45, 46 connected in parallel, and a chamber 47 connected in parallel to the valves and which is divided in two parts by a control diaphragm 48, as shown in FIG. 3. When gas is flowing through one or the other of the one-way valves 45, 46, according to the direction of flow in the conduit 39, the pressure drop across the one-way valve concerned causes the diaphragm 48 to be pressed in the flow direction of the gas. This is utilized to control the dosing means 13, so that it discharges the gas quantity in the reservoir 40 into the breathing bag 1 (through the valve 43) each time when, during exhalation, there is not achieved a sufficient filling of the breathing bag. For this purpose the control diaphragm 48 is coupled to an operating rod 49 which is moved to the right and affects the lever 44 when the diaphragm 48 is pressed to the right and opens the valve 43, provided that the movement of the operating rod 49 is not prevented as a result of a "blocking signal" delivered from the sensing means 14. As mentioned above, this blocking signal is provided from the valve 20. This is connected to the pressurized gas source 11 through a conduit 50, the upper cylinder compartment 36a of the actuator cylinder 36 and the conduit 38, and is further connected through a conduit 51 to a cylinder/piston unit 52 arranged in the dosing means 13 and having a spring-loaded blocking piston 53 and an associated venting valve 54. The blocking signal consists in that the blocking piston 53 is pressure-actuated by opening of the valve 20, so that the piston is moved to the left and actuates a blocking lever 55 preventing said movement of the operating rod 49 even if the control diaphragm 48 is pressed to the right. The blocking signal is nullified in that the control diaphragm 48 is pressed to the left, so that the blocking lever 55 is pivoted by actuation from the operating rod 49 and opens the venting valve 54, so that the blocking piston 53 by spring influence is returned to its initial position.

The operation of the breathing system will be further described below.

As soon as the user of the system starts inhalation, the pressure in the chamber 25 of the mode regulator 10 falls so that the sensing diaphragm 23 is pressed towards the chamber and opens the valve 32. Thereby venting of gas from the lower cylinder compartment **36*b* of the actuator 9 starts, so that the actuator contracts the side faces of the breathing bag 1, so as to maintain a certain safety overpressure in the breathing mask 2. With exhalation the pressure in the breathing mask rises, and this pressure increase is transferred through a passage 56 to the chamber 25 of the mode regulator, so that the sensing diaphragm 23 is pressed outwards towards the chamber 24. Thereby the valve 33 is opened, so that the lower cylinder compartment of the actuator 9** is supplied with compressed gas (oxygen) from the pressurized gas source.

The main supply of oxygen to the breathing bag takes place through the venting valve 32 of the mode regulator.

Since the actuator as mentioned is dimensioned so as to supply a bit too little oxygen, the dosing means 13 also injects the metered oxygen quantity from the reservoir 40 to the breathing bag 1 after each exhalation wherein the breathing bag has not been sufficiently filled with breathing gas. The injection of oxygen takes place at the same time as oxygen is vented from the actuator, and the control diaphragm 48 is pressed to the right and opens the valve 43 by way of the operating rod 49 and the lever 44, that is, just after the inhalation phase has started. The condition for opening of the valve 43 is that the sensing means 14 has not delivered a "blocking signal", which signal is delivered from the valve 20 when the lever 18 is lifted by the transverse pin 19 on the arm 16. As mentioned above, the blocking signal disables the control diaphragm 48 from moving the lever 44 to the right and opening the valve 43. The blocking signal is nullified automatically when the breathing bag again gets into the exhalation mode and the diaphragm 48 is pressed to the left and opens the venting valve 54.

In the embodiment described above it has been emphasized that the equipment is to be completely "closed", since this gives advantages with respect to safety in inflammable surroundings. In principle, there is nothing to prevent that the equipment is made "semi-closed", for example with a view to sports diving. In that case it is natural to take as one's basis that the oxygen supply through the pneumatic actuator is larger than the consumption, and that an automatic means is constructed which dumps gas each time the breathing bag in exhalation is filled beyond a given level. Further, it is conceivable that the pneumatic assistance is based on gas supply from one gas reservoir, and that the compensation of oxygen takes place from another one, without this having to change the structure to a substantial degree.

In cases where the system according to the invention is to be used in a gas-filled atmosphere, it is natural, because of weight, size, etc., to build the mode regulator into the breathing bag, as shown and described. In connection with e.g. diving, hydrostatic conditions will make it natural to build the mode regulator into the breathing mouthpiece or breathing mask. The breathing system will be operative as soon as the reducing valve supplies gas to the pneumatics of the system.

As regards the arrangement for cooling-down of the breathing gas, it will be clear that this may be applied for virtually all types of breathing systems used in gas-filled surroundings.

I claim:

1. A breathing system, especially for use in an atmosphere containing toxic gases, wherein exhaled gas is at least partly recirculated, said system comprising:

- a circulation circuit;
- a breathing piece for application to the face of a user;
- absorption means for absorbing exhaled $CO_2$;
- a pneumatically controlled breathing bag communicating in said circulation circuit with said breathing piece and said absorption means;
- a pneumatic actuator arranged for alternating expansion and contraction of said breathing bag in accordance with the breathing pattern of the user;
- a pressurized gas source coupled to said breathing bag to supplement the breathing gas therein;
- a mode regulator arranged to control the actuator's expansion and contraction of the breathing bag, and to supply breathing gas to said breathing bag, by selectively supplying breathing gas from said pressurized gas source to said actuator, and by venting breathing gas from said actuator to said breathing bag; and dosing means for supplementing the breathing gas supplied to the breathing bag by said mode regulator, said dosing means comprising a separate gas reservoir connected to said pressurized gas source, said dosing means supplying a metered gas quantity contained in said separate gas reservoir to said breathing bag responsive to the degree of filling of the bag by said mode regulator.

2. A breathing system according to claim 1, wherein said circulation circuit comprises lengths of conduit covered by a relatively thick porous material which, when saturated with water, utilizes the evaporation of the water for cooling down the breathing gas circulating in the circulation circuit during operation.

3. A breathing system according to claim 1 or 2, wherein:

said mode regulator comprises a valve arrangement and a sensing diaphragm cooperating therewith, said sensing diaphragm having first and second sides, said first side being influenced by the surrounding atmospheric pressure, said second side being influenced by the gas pressure in said breathing piece; and movement of said sensing diaphragm from a central position is transferred to said valve arrangement which, in dependence on the movement direction of the diaphragm, either opens to supply pressurized gas to said actuator, or vents the actuator.

4. A breathing system according to claim 3, wherein said first side of the sensing diaphragm is also influenced by a spring mechanism for maintaining an overpressure in said breathing piece relative to the surroundings.

5. A breathing system according to claim 4, wherein the spring force of said spring mechanism is adjustable, for adjustment of the overpressure in the breathing piece.

6. A breathing system according to claim 1, wherein said actuator comprises a cylinder/piston unit coupled to said pressurized gas source through said mode regulator, said mode regulator including a valve arrangement comprising a first valve which is opened for venting of said actuator, and a second valve which is opened to supply pressurized gas to the actuator.

7. A breathing system according to claim 6, wherein the piston of said actuator has opposite pressure surfaces with substantially different areas, the smallest pressure surface being under constant pressure influence from said pressurized gas source, so that a pressure direction of said actuator changes as the opposite surface of said piston is supplied with gas from the pressurized gas source or is vented.

8. A breathing system according to claim 6, wherein said gas reservoir is connected to said pressurized gas source through a third valve and to the interior of said breathing bag through a fourth valve, said third and fourth valves being arranged to be actuated by a common operating member, and wherein a control diaphragm is arranged in a conduit connection between said valve arrangement of said mode regulator, and said actuator, said diaphragm being coupled to said operating member and serving to open said fourth valve during venting of the actuator through said first valve.

9. A breathing system according to claim 8, including a sensing means for sensing whether there is sufficient gas in the breathing system, and which, in case a chosen degree of filling of said breathing bag is exceeded, is arranged to actuate a blocking means for then preventing said common operating member of said dosing means from opening said fourth valve.

10. A breathing system according to claim 9, wherein said sensing means comprises a fifth valve and said blocking means comprises a pneumatic piston coupled to said pressurized gas source through said fifth valve.

11. A breathing system, especially for use in an atmosphere containing toxic gases, wherein exhaled gas is at least partly recirculated, said system comprising:

a circulation circuit;

a breathing piece for application to the face of a user;

absorption means for absorbing exhaled $CO_2$;

a pneumatically controlled breathing bag communicating in said circulation circuit with said breathing piece and said absorption means;

a pneumatic actuator arranged for alternating expansion and contraction of said breathing bag in accordance with the breathing pattern of the user;

a pressurized gas source coupled to said breathing bag to supplement the breathing gas therein;

a mode regulator arranged to control the actuator's expansion and contraction of the breathing bag while simultaneously maintaining an overpressure in said breathing piece, relative to the surroundings; and dosing means for supplying a metered gas quantity to said breathing bag in dependence on the degree of filling of the bag;

wherein:

said mode regulator comprises a valve arrangement and a sensing diaphragm cooperating therewith, said sensing diaphragm having first and second sides, said first side being influenced by the surrounding atmospheric pressure and by a spring mechanism for maintaining said overpressure in the breathing piece, said second side being influenced by the gas pressure in said breathing piece; and movement of said sensing diaphragm from a central position is transferred to said valve arrangement which, in dependence on the movement direction of the diaphragm, either opens to supply pressurized gas to said actuator, or vents the actuator.

12. A breathing system according to claim 11, wherein the spring force of said spring mechanism is adjustable, for adjustment of the overpressure in the breathing piece.

13. A breathing system, especially for use in an atmosphere containing toxic gases, wherein exhaled gas is at least partly recirculated, said system comprising:

a circulation circuit;

a breathing piece for application to the face of a user;

absorption means for absorbing exhaled $CO_2$;

a pneumatically controlled breathing bag communicating in said circulation circuit with said breathing piece and said absorption means;

a pneumatic actuator arranged for alternating expansion and contraction of said breathing bag in accordance with the breathing pattern of the user;

a pressurized gas source coupled to said breathing bag to supplement the breathing gas therein;

a mode regulator arranged to control the actuator's expansion and contraction of the breathing bag while simultaneously maintaining an overpressure in said breathing piece, relative to the surroundings; and dosing means for supplying a metered gas quantity to said breathing bag in dependence on the degree of filling of the bag;

said actuator comprising a cylinder/piston unit coupled to said pressurized gas source through said mode regulator, said mode regulator including a valve arrangement comprising a first valve which is opened for venting said actuator, and a second valve which is opened to supply pressurized gas to the actuator.

14. A breathing system according to claim 13, wherein the piston of the actuator has opposite pressure surfaces with substantially different areas, the smallest pressure surface being under constant pressure influence from said pressurized gas source, so that a pressure direction of said actuator changes as the opposite surface of said piston is supplied with gas from the pressurized gas source or is vented.

15. A breathing system according to claim 13, wherein said dosing means comprises a gas reservoir which is connected to said pressurized gas source through a third valve and to the interior of said breathing bag through a fourth valve, said third and fourth valves being arranged to be actuated by a common operating member, and wherein a control diaphragm is arranged in a conduit connection between said valve arrangement of said mode regulator, and said actuator, said diaphragm being coupled to said operating member and serving to open said fourth valve during venting of the actuator through said first valve.

16. A breathing system according to claim 15, including a sensing means for sensing whether there is sufficient gas in the breathing system in which, in case a chosen degree of filling of said breathing bag is exceeded, is arranged to actuate blocking means for preventing said common operating member of said dosing means from opening said fourth valve.

17. A breathing system according to claim 16, wherein said sensing means comprises a fifth valve and said blocking means comprises a pneumatic piston coupled to said pressurized gas source through said fifth valve.

* * * * *